(12) United States Patent
Camden et al.

(10) Patent No.: US 6,194,430 B1
(45) Date of Patent: Feb. 27, 2001

(54) VIRAL TREATMENT

(75) Inventors: James Berger Camden, West Chester; Joseph Herman Gardner, Cincinnati; David Thomas Stanton, Hamilton, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/538,006

(22) Filed: Mar. 29, 2000

Related U.S. Application Data

(63) Continuation-in-part of application No. 09/281,892, filed on Mar. 31, 1999, now abandoned.

(51) Int. Cl.$^7$ .................................................. A61K 31/437
(52) U.S. Cl. ............................................................. 514/303
(58) Field of Search ............................................. 514/303

(56) References Cited

U.S. PATENT DOCUMENTS 3,590,045  6/1971  Vogt .................................... 260/295

FOREIGN PATENT DOCUMENTS

3722992  *  1/1989  (DE) .
1318859  5/1973  (GB) .

OTHER PUBLICATIONS

Garmaise, et al., *J. Org. Chem,*., 1964, vol. 29, p. 3403.
Vanden Eynde, et al., *Bull. Soc. Chim. Belg.*, 1993, vol. 102, No. 5, p. 357.
Chemical Abstracts 82:4256, Kristinsson et al., Methyl [3–carbzmoyl–3H–imidazo [4,5–b] pyridin–2–yl] carbamates, Sep. 12, 1974.
Chemical Abstracts 77:34513, Brody et al., Anthelmintic alkyl 1(3)H–imidazo [4,5–b] pyridine–2–carbamates, Apr. 20, 1972.
Chemical Abstracts 87:167987, Kempter, et al., sym-–Hexahydrotriazino [1,2–a] benzimidazoles and hetero analogs, 1977.
Coates, et al., *J. Med. Chem.*, 1993, 36, 1386–1392.
Katagiri, et al., *J. Org. Chem.*, 1982, 47, 169–170.
Dubey, et al., *Indian Journal of Chemistry*, vol. 18B, Nov. 1979, pp. 428–431.
Utilov, et al., *Khimiya Geterotsiklicheskikh Soedinenii*, 1987, N5, pp. 639–645 with translation.

\* cited by examiner

*Primary Examiner*—Phyllis G. Spivack
(74) *Attorney, Agent, or Firm*—Rose Ann Dabek; Steven W. Miller

(57) ABSTRACT

A pharmaceutical composition is disclosed to treat viral infections, particularly HIV and hepatitis, as well as to treat fungal infections of the genus *cryptococcus neoformans* or *curvularai lunata*. The composition comprises from about 10 mg to about 6000 mg of a 2-thienyl-imidazolo [4,5] pyridine of the formula:

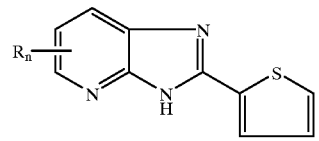

wherein n is from 1 to 4, R is selected from the group consisting of hydrogen, alkyl having from 1 to 7 carbon atoms, chloro, bromo or fluoro, oxychloro, hydroxy, sulfhydryl, alkoxy having the formula —O(CH$_2$)$_y$CH$_3$ wherein y is from 1 to 6, the prodrugs thereof, and the pharmaceutically acceptable salts thereof. The preferred anti-viral compound is

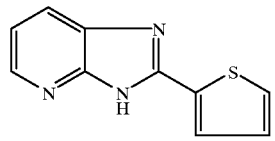

or its hydrochloride salt.

43 Claims, No Drawings

VIRAL TREATMENT

This application is a continuation in part of application of J. B. Camden. Ser. No. 09/281,892, filed Mar. 31, 1999 abandonded.

TECHNICAL FIELD

This invention is treatment of viral infections, in animals, particularly in mammals with a pharmaceutical composition containing one or more 2-thienyl-imidazolo [4,5]pyridine compounds. This invention is a pharmaceutical composition that is effective against the treatment of viruses. The composition can be used to treat viral infections, notably hepatitis, including hepatitis C virus (HCV) hepatitis B virus (HBV), human immunodeficiency syndrome (HIV), and Kaposi sarcoma.

BACKGROUND OF THE INVENTION

HIV and other viral infections such as hepatitis are a few of the leading causes of death. HIV is the virus known to cause acquired immunodeficiency syndrome (AIDS) in humans. HIV is a disease in which a virus is replicated in the body or in host cells. The virus attacks the body's immune system.

Several drugs have been approved for treatment of this devastating disease, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, *Science*, 260(5112), 1286–1293 (1993) and D. D. Richman, *Science*, 272(5270), 1886–1888 (1996). An AIDS vaccine (Salk's vaccine) has been tested and several proteins which are chemokines from CD8 have been discovered to act as HIV suppressors. In addition to the above synthetic nucleoside analogs, proteins, and antibodies, several plants and substances derived from plants have been found to have in vitro anti-HIV activity. However, HIV virus is not easily destroyed nor is there a good mechanism for keeping the host cells from replicating the virus.

Thus, medical professionals continue to search for drugs that can prevent HIV infections, treat HIV virus carriers to prevent their diseases from progressing to full-blown deadly AIDS, and to treat the AIDS patient.

Herpes simplex virus (HSV) types 1 and 2 are persistent viruses that commonly infect humans; they cause a variety of troubling human diseases. HSV type 1 causes oral "fever blisters" (recurrent herpes labialis), and HSV type 2 causes genital herpes, which has become a major venereal disease in many parts of the world. No fully satisfactory treatment for genital herpes currently exists. In addition, although it is uncommon, HSV can also cause encephalitis, a life-threatening infection of the brain. (*The Merck Manual*, Holvey, Ed., 1972; Whitley, Herpes Simplex Viruses, In: *Virology*, 2nd Ed., Raven Press (1990)). A most serious HSV-caused disorder is dendritic keratitis, an eye infection that produces a branched lesion of the cornea, which can in turn lead to permanent scarring and loss of vision. Ocular infections with HSV are a major cause of blindness. HSV is also a virus which is difficult, if not impossible to cure.

Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with avirion size of 42 nm. HCV is a RNA virus with a virion size of 30–60 nm. See D. S. Chen, *J. Formos. Med. Assoc.*, 95(1), 6–12 (1996).

Hepatitis C infects 4 to 5 times the number of people infected with HIV. Hepatitis C is difficult to treat and it is estimated that there are 500 million people infected with it worldwide (about 15 time those infected with HIV). No effective immunization is currently available, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment and or ribavarin which can inhibit viral replication in infected cells and also improve liver function in some people. Treatment with interferon with or without Ribavarin however has limited long term efficacy with a response rate about 25%.

Hepatitis B virus infection lead to a wide spectrum of liver injury. Moreover, chronic hepatitis B infection has been linked to the subsequent development of hepatocellular carcinoma, a major cause of death. Current prevention of HBV infection is a hepatitis B vaccination which is safe and effective. However vaccination is not effective in treating those already infected (i.e., carriers and patients). Many drugs have been used in treating chronic hepatitis B and none have been proven to be effective, except interferon.

Treatment of HCV and HBV with interferon has limited success and has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Because the interferon therapy has limited efficacy and frequent adverse effects, a more effective regimen is needed.

In the present invention it has been discovered that the compounds described above are useful for the treatment of hepatitis C virus, hepatitis B virus, herpes simplex and the treatment of HIV infection and other viral infections.

SUMMARY OF THE INVENTION

A pharmaceutical composition for treatment of viral infections in patients in need thereof, and in particular, warm blooded animals and humans, comprising a pharmaceutical carrier and an effective amount anti-viral compound selected from the group consisting of:

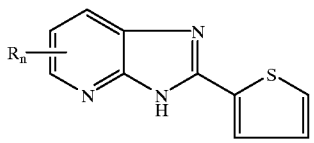

wherein n is 1–3, R is selected from the group consisting of hydrogen, alkyl having from 1 to 7 carbon atoms, chloro, bromo or fluoro, oxychloro, hydroxy, sulfhydryl, and alkoxy having the formula —O(CH$_2$)$_y$CH$_3$ wherein y is from 0 to 6, its prodrugs and pharmaceutically acceptable addition salts.

The preferred material is:

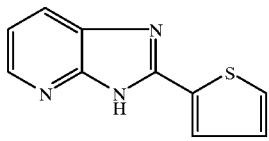

or its pharmaceutical addition salts, in particular the hydrochloride salt.

In the present invention it has been discovered that the anti-viral 2-thienyl-imidazolo [4,5]pyridine compounds are useful for the inhibition of HIV and the treatment of HIV infection as well as in the treatment of hepatitis B infections. The present invention also provides methods for the treatment of HIV infection comprising administering to a host infected with HIV a pharmaceutically or therapeutically effective amount of a anti-viral compound as described herein.

These materials are active against *Cryptococcus neoformas* and *Curvularia lunata*. Both of these are fungi which are found in AIDS patients.

The compositions can be used in conjunction with other treatments for treating viral infections.

The drug can be given daily in one or more doses or from 1 to 4 times a week.

DETAILED DESCRIPTION OF THE INVENTION

A. DEFINITIONS

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention.

By "therapeutically effective amount" is meant an amount of a compound of the present invention effective to yield the desired therapeutic response. For example to inhibit HIV infection or treat the symptoms of infection in a host. The specific safe and effective amount or therapeutically effective amount will, obviously, vary with such factors as the particular condition being treated, the physical condition of the patient, the type of mammal or animal being treated, the duration of the treatment, the nature of concurrent therapy (if any), and the specific formulations employed and the structure of the anti-viral compounds or its derivatives.

As used herein, a "pharmaceutical addition salt or salts" is salt of the thienyl-imidazolo [4,5]pyridine compound which is modified by making acid or base salts of the anti-viral compounds. Examples of pharmaceutically acceptable salts include, but are not limited to, mineral or organic acid salts of basic residues such as amines; alkali or organic salts of acidic residues such as carboxylic acids. Preferably the salts are made using an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the thienyl imidazolo [4,5]pyridine derivatives to the animal or human. The carrier may be liquid or solid and is selected with the planned manner of administration in mind.

As used herein, the "thienyl-imidazolo [4,5]pyridine derivatives" or "2-thienyl-imidazolo [4,5]pyridine compounds" or "2-(2-thienyl)imidazolo[4,5-b]pyridine compounds are derivatives" are the members of the group of compounds having the formula:

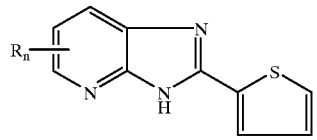

wherein n is 1–3, R is selected from the group consisting of hydrogen, alkyl having from 1 to 7 carbon atoms, chloro, bromo or fluoro, oxychloro, hydroxy, sulfhydryl, and alkoxy having the formula —O(CH$_2$)$_y$CH$_3$ wherein y is from 1 to 6, its prodrugs and pharmaceutically acceptable addition salts.

As used herein "alkyl" includes straight, branched chain and cyclic alkanes. "Prodrugs" are considered to be any covalently bonded carriers which release the active parent drug according to the formula of the thienyl imidazolo [4,5]pyridine compounds described above in vivo when such prodrug is administered to a mammalian subject. Prodrugs of the thienyl imidazolo [4,5]pyridine compounds are prepared by modifying functional groups present in the compounds in such a way that the modifications are cleaved, either in routine manipulation or in vivo to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the thienyl imidazolo [4,5]pyridine derivatives; formamide, acetamide and benzamide derivatives of the amino group; phosphate esters, dimethylglycine esters, aminoalkylbenzyl esters, aminoalkyl esters and carboxyalkyl esters of alcohol and phenol functional groups in the thienyl imidazolo [4,5]pyridine derivatives; and the like.

Further protecting groups include carboxyl protecting groups disclosed in "Protective Groups in Organic Synthesis" (by Green & Wuts, 1999, 3rd Ed.); "Protecting Groups (Tieme Foundations Organic Chemistry Series N Group" (by Kocienskie; Tieme Medical Publishers; 1994), the relevant disclosures of which are hereby incorporated by reference.

As used herein, "anti-viral compounds" are thienyl-imidazolo [4,5]pyridine derivatives, and preferably, 2-(2-thienyl)-imidazolo [4,5]pyridine or the pharmaceutically acceptable acid addition salts or prodrugs thereof.

As used herein "viruses" includes viruses which infect animals or mammals, including humans. Viruses include retroviruses, HIV, influenza, polio viruses, herpes simplex, hepatitis B, hepatitis C, other hepatitis viruses, Kaposi's sarcoma virus, rhinoviruses, bovine diarrhea virus, and the like. HIV and AIDS are immunosuppressant diseases.

As used herein "combination therapy" means that the patient in need of the drug is treated or given another drug for the disease in conjunction with the 2-thienyl-imidazolo [4,5]pyridine derivatives. This combination therapy can be sequential therapy where the patient is treated first with one or more drugs and then the other, or two or more drugs are given simultaneously.

B. THE ANTI-VIRAL COMPOUNDS

The 2-thienyl-imidazolo [4,5]pyridine compounds useful herein have the formula:

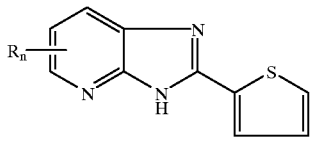

wherein n is 1–3, R is selected from the group consisting of hydrogen, alkyl having from 1 to 7 carbon atoms, chloro, bromo or fluoro, oxychloro, hydroxy, sulfhydryl, alkoxy having the formula —O(CH$_2$)$_y$CH$_3$ wherein y is from 0 to 6, preferably from 1 to 6. Preferably the 2-(2-thienyl)imidazolo [4,5-b]pyridine is substituted with an alkyl of less than 4 carbons, a halogen, preferably a chloro, nitro, hydroxy or oxychloro in the 7 or 8 position and the remaining substituents of the pyridine ring are hydrogen.

The preferred antiviral agent is 2-(2-thienyl) imidazolo [4,5-b]pyridine:

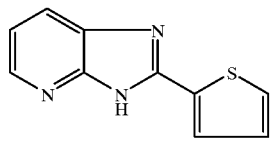

or its pharmaceutical addition salts.

C. SYNTHESIS

The thienyl imidazolo [4,5]pyridine derivatives can be prepared in a number of ways well known to one skilled in the art of organic synthesis. Thienyl imidazolo [4,5]pyridine derivatives can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

A general synthesis route begins with 2-chloropyridine which is nitrated in the presence of sulfuric acid to make 2-chloro-3-nitropyridine. This material is reacted with ammonium acetate in the presence of diglyme at about 160° C. to form 2-amino-3-nitropyridine which is reduced to form 2,3-diaminopyridine. The 2,3-diaminopyridine is reacted with 2-thiophenecarboxylic acid in the presence of polyphosphoric acid at about 125° C. to prepare 2-(2-thienyl) imidazolo [4,5]pyridine.

The preparation of 2-(2-thienyl)-imidazolo [4,5]pyridine is described in Germaise, et al. *J. Org. Chem.*, 1964, vol. 29, 3403 and Vanden Eynde, et al., *Bull. Soc. Chem. Belg.*, vol. 2, No. 5 (1993). Coates, *J. Medicine*, 1993, vol. 36, pp. 1387–1392 describes the synthesis of other imidazolo [4,5] pyridine derivatives.

The pharmaceutically acceptable salts of the present invention can be synthesized from the thienyl imidazolo [4,5]pyridine derivatives which contain a basic or acidic moiety by conventional chemical methods. Generally, such salts can be prepared by reacting the free acid or base forms of these anti-viral compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The pharmaceutically acceptable salts of the thienyl imidazolo [4,5]pyridine compounds include the conventional non-toxic salts or the quaternary ammonium salts of the thienyl imidazolo [4,5]pyridine derivatives formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

D. DOSAGE

Any suitable dosage may be given in the method of the invention. The type of carrier and the amount will vary widely depending on the species of the warm blooded animal or human, and virus being treated. The dosage administered will, of course, vary depending upon known factors, such as the pharmacodynamic characteristics of the particular agent and its mode and route of administration; the age, health and/or weight of the recipient; the nature and extent of the symptoms; the metabolic characteristics of the drug and patient, the kind of concurrent treatment; the frequency of treatment; or the effect desired.

The thienyl imidazolo [4,5]pyridine is preferably micronized or powdered so that it is more easily dispersed and solubilized by the body. Processes for grinding or pulverizing drugs are well known in the art. For example, a hammer mill or similar milling device can be used. The preferred particle size is less than about 100μ and preferably less than 50μ.

Generally a dosage of as little as about 1 milligrams (mg) per kilogram (kg) of body mass is suitable, but preferably as little as 10 mg/kg and up to about 10,000 mg/kg can be used. Preferably from 10 mg/kg to about 5000 mg/kg is used. Most preferably the doses are between 250 mg/kg to about 5000 mg/kg Doses useful in the treatment of viral infections are 250 mg/kg, 500 mg/kg, 2500 mg/kg, 3500 mg/kg, 4000 mg/kg. 5000 mg/kg and 6000 mg/kg. Any range of doses can be used. Generally 2-thienyl-imidazolo [4,5]pyridine derivatives can be administered on a daily basis one or more times a day, or 2-thienyl-imidazolo [4,5]pyridine derivatives can be given one to four times a week either in a single dose or separate doses during the day. Twice weekly dosing over a period of at least several weeks is preferred, and often dosing will be continued over extended periods of time and maybe for the lifetime of the patient. However, the dosage and the dosage regimen will vary depending on the ability of the patient to sustain the desired and effective plasma levels of the anti-viral agents in the blood.

Intravenously, the most preferred doses may range from about 1 to about 10 mg/kg/minute during a constant rate infusion.

The dosage for humans is generally less than that used in mice and is typically about 1/12 of the dose that is effective in mice. Thus, if 500 mg/kg was effective in mice, a dose of 42 mg/kg would be used in humans. For a 60 kg man, this dose would be 2520 mg.

The anti-viral compounds are generally safe. The $LD_{50}$ is fairly high, about 1500 mg/kg given orally in mice and there are no special handling requirements. The anti-viral compounds can be given orally, and as they are not very soluble, they are preferably given in tablet form or as a suspension.

E. METHOD OF ADMINISTERING AND DOSAGE DELIVERY FORMS

The compounds of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into or around the virus.

The dosage amounts are based on the effective inhibitory concentrations observed in anti-viral studies. The preferred route will vary with the (1) condition and age of the recipient, (2) virus being treated (3) nature of the infection and (4) desired blood levels. It is believed that parenteral treatment by intravenous, subcutaneous, or intramuscular application of the compounds of the present invention formulated with an appropriate carrier, other antiviral agents or compounds or diluents to facilitate application will be the preferred method of administering the compounds to warm blooded animals.

The thienyl imidazolo [4,5]pyridine derivatives are preferably micronized or powdered so that it is more easily dispersed and solubilized by the body. Processes for grinding or pulverizing drugs are well known in the art. For example, a hammer mill or similar milling device can be used. The preferred particle size is less than about 100μ and preferably less than 50μ. These compounds are not very soluble, and therefore are preferably given in tablet form or as a suspension. Suitable methods of administering the compounds of the present invention and dosage forms can be found herein below.

The thienyl imidazolo [4,5]pyridine derivatives of this invention can be administered as treatment for viral infections by any means that produces contact of the active agent with the agent's site of action in the body. They can be administered by any conventional means available for use in conjunction with pharmaceuticals, either as individual therapeutic agents or in a combination of therapeutic. Preferably the compounds of the present invention is administered as a pharmaceutical formulation comprising at least one compound of the present invention, as defined above, together with one or more pharmaceutically acceptable carriers. It can be co-administered in the form of a tablet or capsule, as an agglomerated powder or in a liquid form or as a lipsome.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The thienyl imidazolo [4,5]pyridine compounds or derivatives of the present invention can also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

1. Combination Therapy

The compounds of the present invention may additionally be combined with other antiviral compounds to provide an operative combination. As used herein "combination therapy" means that the patient in need of the drug is treated or given another drug for the disease in conjunction with the thienyl-imidazolo [4,5]pyridine derivatives. This combination therapy can be sequential therapy where the patient is treated first with at least one other drug and then the other, or two or more drugs are given simultaneously. The exact dose and method of administering the combination will depend upon the particular virus being treated and the type and extent of the combination therapy. It is intended to include any chemically compatible combination of a compound of this inventive group with other compounds of the inventive group or other compounds outside of the inventive group, as long as the combination does not eliminate the antiviral activity of the compound of this inventive group. For example, one or more thienyl imidazolo [4,5]pyridine derivatives can be combined with other antiviral agents or potentiators. Potentiators are materials which affect the body's response to the anti-viral agent. In the case of HIV a combination therapy with AZT, TC-3 or protease inhibitors is effective. In the case of hepatitis, cyclovir, famciclovir or valacyclovir, Ribavirin, interferon or combinations of Ribavirin and Interferon or beta globulin is administered as a combination therapy. For herpes, a recombinant alpha interferon can be used as a combination therapy.

In some embodiments, the 2-(2-thienyl) imidazolo[4,5] pyridine compound is used in combination with one or more potentiators and/or antiviral agents for the treatment of viral infections. An exemplary potentiator is triprolidine or its cis-isomer which are used in combination with chemotherapeutic agents and the 2-(2-thienyl) imidazolo[4,5]pyridine compound . Triprolidine is described in U.S. Pat. No. 5,114,951 (1992). Another potentiator is procodazole, 1H-Benzimidazole-2-propanoic acid; [β-(2-benzimidazole) propionic acid; 2-(2-carboxyethyl)benzimidazole; propazol]. Procodazole is a non-specific immunoprotective agent active against viral and bacterial infections that is used with the compositions claimed herein. It is effective with the 2-(2-thienyl) imidazolo[4,5]pyridine compound in treating viral infections. Procodazole can also be combined with the 2-thienyl imidazolo[4,5]pyridine compound and other antiviral agents. Other potentiators which can be used with 2-(2-thienyl) imidazolo[4,5-b]pyridine compounds include monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl)ethylenediamine, leucovorin, heparin, N-[4-[(4-fluorphenyl)sulfonly]phenyl] acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide.

In some embodiments of the invention, a 2-(2-thienyl) imidazolo[4,5]pyridine compound is used in combination with one or more other therapeutic agents, such as anti-inflammatory, anti-viral, anti-fungal, amoebicidal, trichomonocidal, analgesic, anti-neoplastic, anti-hypertensives, anti-microbial and/or steroid drugs, to treat antiviral infections. In some preferred embodiments, patients with viral infections are treated with a combination of one or more 2-(2-thienyl) imidazolo[4,5]pyridine compounds with one or more of beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof.

The combination therapy can be sequential, that is the treatment with one agent first and then the second agent, or it can be treatrnent with both agents at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the infection and the response to the treatment.

2. Unit Dosage

The compounds of the present invention may administered in a unit dosage form and may be prepared by any methods well known in the art. Such methods include combining the compounds of the present invention with a carrier or diluent which constitutes one or more accessory ingredients. Typically, the formulations are prepared by uniformly mixing the active ingredient with liquid carriers or finely divided solid carriers or both. and then if necessary shaping the product. A pharmaceutical carrier is selected on the basis of the chosen route of administration and standard pharmaceutical practice. Each carrier must be "acceptable" In the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Dosage forms (compositions suitable for administration) comprise from about 1 milligram to about 1000 milligrams of active ingredient per dosage unit. Preferably the dosage forms will contain from about 10 mg to about 500 mg. In these pharmaceutical compositions the active ingredient will ordinarily be present in an amount of about 0.5 to about 95% by weight based on the total weight of the dosage unit.

3. Pharmaceutical Kits

The present invention also includes pharmaceutical kits useful, for example, for the treatment of hepatitis infection, which comprise one or more containers containing a pharmaceutical composition comprising a therapeutically effective amount of a thienyl imidazolo [4,5]pyridine derivatives. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit. In the present disclosure it should be understood that the specified materials and conditions are important in practicing the invention but that unspecified materials and conditions are not excluded so long as they do not prevent the benefits of the invention from being realized.

Specific examples of pharmaceutical acceptable carriers and excipients that may be used to formulate oral dosage forms of the present invention are described in U.S. Pat. No. 3,903,297 to Robert, issued Sep. 2, 1975.

Techniques and compositions for making dosage forms useful in the present invention are described herein below.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary or paste.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin and cyclodextrin derivatives and the like.

Capsule or tablets can be easily formulated and can be made easy to swallow or chew. Tablets may contain suitable binders, lubricants, diluents, disintegrating agents, coloring agents, flavoring agents, flow-inducing agents, and melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethlcellose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Molded tables may be made by molding in a suitable machine a mixture of the powdered active ingredient moistened with an inert liquid diluent.

The tablets may optionally be coated or scored and may be formulated so as to provide slow or controlled release of the active ingredient. Tablets may also optionally be provided with an enteric coating to provide release in parts of the gut other than the stomach.

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound which enhances absorption or penetration of the active ingredient through the skin or other affected areas. Examples of such dermal penetration enhancers include dimethylsulfoxide and related analogues.

The oil phase of the emulsions of the composition used to treat subjects in the present invention may be constituted from known ingredients in a known manner. This phase may comprise one or more emulsifiers. For example, the oily phase comprises at least one emulsifier with a fat or an oil or with both a fat and an oil or a hydrophilic emulsifier is included together with a lipophilic emulsifier which acts as a stabilizer. Together, the emulsifier(s) with or without stabilizer(s) make up an emulsifying was, and the wax together with the oil and/or fat make up the emulsifying ointment base which forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono-or dibasic alkyl esters, mineral oil. The choice of suitable oils or fats for the formulation is based on achieving the desired cosmetic properties, the properties required and compatibility with the active ingredient.

The compounds may also be administered vaginally for example, as pessaries, tampons, creams, gels, pastes, foams or spray formulations containing in addition to the active ingredient. Such carriers are known in the art.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous isotonic with the blood of the intended recipient; and aqueous and non-aqueous sterile suspensions which may include suspending systems which are designed to target the compound to blood components or one or more organs. The formulations may be presented in unit-dose or multi-dose sealed containers, for example, ampoules and vials. Extemporaneous injections solutions and suspensions may be prepared from sterile powders, granules and tablets of the kind previously described. Liposomes are preferred for intravenous administration of the 2-thienyl-imidazolo-[4,5-b] pyridine compound.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Intravenously, the most preferred doses can range from about 1 to about 10 mg/kg/minute during a constant rate infusion. Thienyl imidazolo [4,5]pyridine derivatives can be administered in a single daily dose, or the total daily dosage can be administered in divided doses of two, three, or four times daily. The thienyl imidazolo [4,5]pyridine derivatives can be given in one or more doses on a daily basis or from one to three times a week.

The present invention additionally include administering compounds of the herein described formula for the use in the form of veterinary formulations, which may be prepared, for example, by methods that are conventional in the art.

Useful pharmaceutical dosage forms for administration of the compounds of this invention are illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams of magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

F. METHOD OF TREATMENT

The method of treatment can be any suitable method which is effective in the treatment of the particular virus or viral infection that is being treated. Treatment includes administering a therapeutically effective amount of the compounds of the present invention in a form described herein above, to a subject in need of treatment. As previously described, the composition can be administered oral, rectal, topical, vaginally, nasally, parenterally, intravenously and the like. The method of applying an effective amount varies depending on the viral infection being treated and the desired blood level. It is believed that parenteral treatment by intravenous, subcutaneous, or intramuscular application of thienyl imidazolo [4,5]pyridine derivatives, formulated with an appropriate carrier, additional viral inhibiting compound or compounds or diluent to facilitate application will be the preferred method of administering the compounds to mammals or warm blooded animals.

Mechanism

The mechanism of action of the 2-(2-thienyl)-imidazolo [4,5-b]pyridine derivatives is not known. Neither 2-(2-thienyl)-imidazolo [4,5-b]pyridine or its hydrochloride salt showed activity as a protease inhibitor when screened using a fluorometric method or as an integrase inhibitor. These results are summarized in the following tables. 2-Thienyl-imidazolo [4,5]pyridine hydrochloride salt autofluoresces and may cause some interference with this test.

Protease Inhibition Assay

Protease inhibition is evaluated using a fluorometric method. Enzyme (Bachem) is diluted to 116 $\mu$gm/ml in 50 mM NaOAC, 5 mM DTT, 2 mM EDTA, 10% glycerol (pH 5.0) and stored as 10 $\mu$l samples at −20° C., HIV protease substrates I (Molecular Probes) is diluted to a working concentration of 0.32 nmoles/$\mu$l. Enzyme (20 $\mu$l) and drug (20 $\mu$l) are added to each well of a microtiter plate as appropriate. Positive and negative controls are evaluated in parallel. Fluorescence is quantitated on Labsystems Fluroskan II using 355 nm/460 nm at 37° C. at time zero and at 30 minute intervals for 2 hours. In instances where autofluorescence precludes use of the fluorometric HIV-1 protease assay or confirmation of a result is required, an HPLC based protease assay can be employed.

Integrase Inhibition Assay

A biochemical integrase assay described by Craigie et at (HIV, vol. 2: A practical Approach) Biochemistry, Molecular Biology and Drug Discovery, Ed. J. Karn 1995) to screen agents for their ability to inhibit HIV-1 integrase. In this system, a kinased oligonucleotide serves as the target of 3' processing and the subsequent strand transfer reaction. The 3' processing reaction involves the removal of 2 nucleotides from the 3' ends of the substrate and this is followed by the strand transfer reaction in which the 3' ends are joined to the exposed 5' ends. The 20 μl reaction mixture contains 25 mM MOPS (pH 7.2), 100 g/ml BSA, 10 mM β-mercaptoethanol, 10% glycerol, 7.5 mM $MnCl_2$, 25 nM (7 ng) substrate (Oligo's Etc., Wilsonville, Oreg.) and 200 nM (128 ng) integrase (NIAID AIDS Research and Reference Reagent Program, Bethesda, Md.). The reaction proceeds at 37° C. for 1–2 hours and is terminated by the addition of 20 μl of sequencing stop solution (USB Amersham, Arlington Heights, Ill.). The reaction products are visualized by autoradiography following electrophoresis in 15% polyacrylamide 6M Urea gel. The substrate migrates as a 30 mer, the product of 3' processing migrates as an N-2 band and the strand transfer products migrate more slowly at various sizes larger than the substrate.

| Concentration (nM) | 0 | 1 | 10 | 100 | 1000 |
|---|---|---|---|---|---|
| Protease Inhibition by 654021F - a known protease inhibitor | | | | | |
| sample 1 | 30.7 | 26.1 | 29.2 | 26.5 | 10.0 |
| sample 2 | 26.3 | 30.3 | 27.6 | 25.5 | 6.7 |
| mean | 28.5 | 28.2 | 28.4 | 26.0 | 8.3 |
| % no drug control | 100.0 | 99.0 | 99.7 | 91.3 | 29.3 |
| Protease Inhibition by 2-(2-thienyl)-imidazolo [4,5-b]pyridine | | | | | |
| sample 1 | 30.7 | 27.1 | 33.2 | 75.4 | 219.4 |
| sample 2 | 26.3 | 22.4 | 40.2 | 76.8 | 208.2 |
| mean | 28.5 | 24.7 | 36.7 | 76.1 | 213.8 |
| % no drug control | 100.0 | 86.9 | 128.9 | 267.3 | 751.1 |
| Protease Inhibition by 2-(2-thienyl)-imidazolo [4,5-b] pyridine hydrochloride salt | | | | | |
| sample 1 | 30.7 | 29.9 | 36.0 | 85.4 | 245.7 |
| sample 2 | 26.3 | 22.6 | 34.1 | 84.2 | 248.8 |
| mean | 28.5 | 26.3 | 35.0 | 84.8 | 247.3 |
| % no drug control | 100.0 | 92.3 | 123.1 | 298 | 868.6 |

The $EC_{50}$ value is 0.699 μM for 654021.

| Concentration (μg/ml) | 0 | 0.1 | 1 | 10 | 100 |
|---|---|---|---|---|---|
| HIV-1 Integrase Inhibition 2-(2-thienyl)-imidazolo [4,5-b]pyridine | | | | | |
| sample 1 | 9966 | 11155.2 | 10640.4 | 10814.1 | 7639.4 |
| sample 2 | 9149 | 9998.8 | 9568.4 | 10345.1 | 6788.6 |
| mean | 9558 | 10577 | 10104 | 10580 | 7214 |
| % no drug control | 100.0 | 110.7 | 105.7 | 110.7 | 75.1 |
| HIV-1 Integrase Inhibition by 2-(2-thienyl)-imidazolo [4,5-b] pyridine hydrochloride salt | | | | | |
| sample 1 | 9966 | 9338.5 | 11838.2 | 10848.3 | 10212.5 |
| sample 2 | 9149 | 8948.8 | 12550.7 | 13750.3 | 10928.4 |
| mean | 9558 | 9144 | 12194 | 12299 | 10570 |
| % no drug control | 100.0 | 95.7 | 127.6 | 126.7 | 110.6 |
| HIV-1 Integrase Inhibition by TPX - a known integrase inhibitor | | | | | |
| sample 1 | 9966 | 9065.7 | 1944.7 | 3263.1 | |
| sample 2 | 9149 | 7395.6 | 3182.4 | 2708.1 | |
| mean | 9558 | 8231 | 2564 | 2986 | |
| % no drug control | 100.0 | 85.1 | 26.8 | 31.2 | |

The $EC_{50}$ value is 0.648 μM for TPX and >100 μg/ml for both the 2-(2-thienyl)-imidazolo [4,5-b]pyridine and its hydrochloride salt.

The following examples are illustrative and are not meant to be limiting to the invention. The following methods were used in these tests.

Virus Preparation

A pretitered aliquot of virus is removed from the freezer (−80° C.) and allowed to thaw slowly to room temperature in a biological safety cabinet. The virus is resuspended and diluted into tissue culture medium such that the amount of virus added to each well in a volume of 50 μl will be the amount determined to give complete cell killing at 6 days post infection. In general, the virus pools produced with IIIB isolate of HIV required the addition of 5 μl of virus per well. Pools of RF virus were 5 to 10 fold more potent requiring 0.5–1 μl of virus per well. $TCID_{50}$ calculation by endpoint titration in CEM-SS cells indicated that the multiplicity of infection of these assays ranged from 0.005 to 2.5.

Plate Format

The format of the test plate has been standardized. Each plate contains cell control wells (cells only), virus control wells (cells plus virus), drug toxicity control wells (cells plus drug lonely), drug colorimetric control wells (drug only) as well as experimental wells (drug plus cells plus virus).

XTT Staining of Screening Plates

After 6 days (or the experimental period) of incubation at 37° C. in a 5% carbon dioxide incubator the test plates are analyzed by staining with the tetrazolium dye XTT. XTT-tetrazolium is metabolized by the mitochondrial enzymes of metabolically active cells to a soluble formazan product, allowing the rapid quantitative analysis of the inhibition of HIV-induced cell killing by anti-HIV test substances. On day 6 post-infection plates are removed from the incubator and observed. The use of round bottom microtiter plates allows rapid macroscopic analysis of the activity of a given test compound by the evaluation of pellet size. The results of the macroscopic observations were confirmed and enhanced by further microscopic analysis.

XTT solution is prepared daily as a stock of 1 mg/ml in PBS. Phenazine methosulfate (PMS) solution is prepared at 15 mg/ml in PBS and stored in the dark at −20° C. XTT/PMS stock is prepared immediately before use by diluting the PMS 1:100 into PBS and adding 40 μl per ml of XTT solution. Fifty microliters of XTT/PMS is added to each well of the plate and the plate is reincubated or 4 hours at 37° C. Adhesive plate sealers are used in place of the lids, the sealed plate is inverted several times to mix the soluble formazan product and the plate is read spectrophotometrically at 450 nm with a Molecular Devices Vmax plate reader. Percent cell reduction, percent cell viability, $IC_{25,50, \& 95}$ and $TC_{25,50, \& 95}$ can then be calculated.

Reverse Transcriptase Activity Analysis

A microtiter-based reveres transcriptase (RT) reaction is utilized (Buckheit et al (1991) *AIDS Research and Human Retroviruses* 7:295–302). Tritiated thymidine triphosphate (NEN)(TTP) is resuspended in distilled water at 5 Ci/ml. Poly rA and oligo dT are prepared as a stock solution which is kept at −20° C. The RT reaction buffer is prepared fresh on a daily basis and consists of 125 µl 1M EGTA, 125 µl water, 125 µl Triton X-100, 50 µl Tris (pH 7.4), 50 µl 1 MDDT, and 40 µl 1M $MgCl_2$. These three solutions are mixed together in a ratio of 1 part TTP, 2.5 parts poly rA:oligo dT, 2.5 parts reaction buffer and 4 parts distilled water. Ten microliters of this reaction mixture is placed in a round bottom microtiter place and 15 µl of virus containing supernatant is added and mixed. The plate is incubated at 37° C. for 60 minutes. Following reaction, the reaction volume is spotted onto filter mats, washed 6 times for 5 minutes each in a 5% sodium phosphate buffer, 2 times for 1 minute each in distilled water, 2 times for 1 minute each in 70% ethanol, and then dried. The dried filter mat is placed in a plastic sample bag, Betaplate scintillation fluid is added and the bag is heat sealed. Incorporated radioactivity is quantified utilizing a Wallac Microbeta scintillation counter.

Acute infection of most established human cell lines with HIV-1 results in the eventual establishment of a constitutive virus-producing chronically infected cell line. The cells can be passaged for long periods of time in culture without loss of virus production. These cells may be utilized to evaluate the effects of anti-HIV compounds on syncytium formation or to evaluate the effects of anti-HIV compounds on levels of virus production from these cells. Chronically infected cell lines exhibit little or no cell surface CD4 and cannot be super-infected with other isolates of HIV-1. Each of the cells contains an integrated HIV genome or provirus. Chronically infected CEM, H9 and U937 cell lines have been prepared and cultured by Southern Research Institute, Frederick Md. and are available from them.

CEM-SS cells chronically infected with HIV isolate, for example SKI (CEM-SKI) are cultured in RPMI 1640 tissue culture medium supplemented with 10% fetal bovine serum and antibiotics. Selection is performed by culturing the cells in the presence of the compound to be tested in T25 flasks. CEM-SKI or other infected cells with no added drug are used as the control cells. Cells are allowed to grow to a density of approximately 1×106 cells/ml and are then passaged at a 1:10 dilution. After a period of time, usually one week intervals of drug treatment, cells are evaluated to determine if the inhibitory activity of the compound has been affected by treatment of the cells with either compounds. The drug concentration in the flask is then increased two-fold and the cells maintained as above.

The cell populations contain integrated copies of the HIV genome and constitutively produce HIV at relatively high levels or are latently infected and only produce virus after stimulation with phorbol esters, tumor necrosis factor or IL6 (U1 and ACH2). Reductions in virus products were observed when quantifying supernatant reverse transcriptase activity, Toxicity Values are measured by XTT and activity of the compound in the tests is measured by a Reverse Transcriptase analysis.

EXAMPLE 1

HIV

In an in vitro screening test of 2-(2-thienyl)-imidazolo [4,5-b]pyridine against an HIV-2 virus, CEMROD, the following data was obtained. Table 1 shows results of one test and Table 2 gives the results of a duplicate study.

TABLE 1

| Conc. µg/ml | 0 | 0.32 | 1 | 3.2 | 1.0 | 32 | 100 |
|---|---|---|---|---|---|---|---|
| Reverse Transcriptase Activity | | | | | | | |
| sample 1 | 4206 | 5529 | 5086 | 4017 | 2206 | 390 | 68 |
| sample 2 | 4961 | 6435 | 5476 | 4580 | 2190 | 450 | 68 |
| sample 3 | 5829 | 5878 | 5002 | 4005 | 2812 | 382 | 80 |
| average | 4999 | 5947 | 5188 | 4201 | 2403 | 407 | 72 |
| % virus control | 100 | 119 | 103.8 | 84.0 | 48.1 | 8.1 | 1.4 |
| Toxicity Values | | | | | | | |
| sample 1 | 1.164 | 1.091 | 1.135 | 1.040 | 0.916 | 0.310 | 0.087 |
| sample 2 | 1.091 | 1.200 | 1.169 | 1.092 | 0.894 | 0.331 | 0.87 |
| sample 3 | 1.109 | 1.141 | 1.063 | 1.034 | 0.952 | 0.325 | 0.083 |
| average | 1.121 | 1.144 | 1.122 | 1.055 | 0.912 | 0.322 | 0.086 |
| % cell control | 100 | 102 | 100.1 | 94.1 | 81.3 | 28.7 | 7.6 |

TABLE 2

| Conc. µg/ml | 0 | 0.32 | 1 | 3.2 | 1.0 | 32 | 100 |
|---|---|---|---|---|---|---|---|
| Reverse Transcriptase Activity | | | | | | | |
| sample 1 | 4752 | 5725 | 6264 | 5352 | 2531 | 177 | 60 |
| sample 2 | 4989 | 6365 | 6984 | 4054 | 2081 | 241 | 44 |
| sample 3 | 4709 | 4758 | 4251 | 5050 | 2776 | 173 | 28 |
| Average | 4817 | 5616 | 5833 | 4819 | 2463 | 197 | 44 |
| % virus control | 100 | 116.6 | 121.1 | 100.0 | 51.1 | 4.1 | 0.9 |
| Toxicity Values | | | | | | | |
| sample 1 | 0.958 | 1.189 | 1.066 | 1.008 | 0.694 | 0.183 | 0.121 |
| sample 2 | 0.924 | 1.074 | 1.038 | 0.924 | 0.726 | 0.168 | 0.133 |
| sample 3 | 0.962 | 1.000 | 0.980 | 0.881 | 0.633 | 0.145 | 0.130 |
| average | 0.948 | 1.088 | 1.028 | 0.938 | 0.684 | 0.165 | 0.128 |
| % cell control | 100 | 114.7 | 108.4 | 98.9 | 72.2 | 17.4 | 13.5 |

As can be seen at the higher concentrations, the 2-(2-thienyl)-imidazolo [4,5-b]pyridine is not toxic and shows efficacy in treating HIV.

EXAMPLE 2

HIV-1

A long term in vitro study of 2-(2-thienyl)-imidazolo [4,5-b]pyridine against an HIV-1 cell line, CEMSKI, was conducted at three different levels. The results with CEM-SKI cells were reported at weekly intervals. The reverse transcriptase data is summarized below.

| CEMSKI cell line | | | | | | | | |
|---|---|---|---|---|---|---|---|---|
| Day | 4 | 11 | 18 | 25 | 32 | 39 | 46 | 53 |
| No Drug | 3302 | 3483 | 4114 | 4841 | 3588 | 3161 | 4933 | 6392 |
| 7 μg/ml | 2337 | 2695 | 1450 | 2397 | 2803 | 2386 | 3281 | 4542 |
| 15 μg/ml | 281 | 362 | 928 | 717 | 824 | 736 | 497 | 374 |
| 30 μg/ml | 129 | 157 | 88 | 165 | 152 | 164 | 201 | 104 |
| Day | 60 | 67 | 74 | 71 | 88 | 95 | 102 | 109 |
| No Drug | 5139 | 3451 | 5207 | 14417 | 12405 | 24236 | 25760 | 3052 |
| 7 μg/ml | 5247 | 1743 | 3210 | 12277 | 10871 | 21274 | 15073 | 2840 |
| 15 μg/ml | 671 | 932 | 1687 | 3274 | 4925 | 15117 | 13262 | 2190 |
| 30 μg/ml | 324 | 173 | 257 | 867 | 5870 | 956 | 827 | 402 |

This test was run through 242 days and the data remained consistent.

The CEMSKI cell like is a viral strain of the CEMSS cell line.

When the hydrochloride salt of 2-(2-thienyl)-imidazolo [4,5-b]pyridine was tested in the same manner, similar results were obtained through 60 days.

EXAMPLE 3

CEMRF

A long term in vitro study of 2-(2-thienyl)-imidazolo [4,5-b]pyridine against an HIV-1 cell line, CEMRF, was conducted at three different levels. The results with CEMRF cells were reported at weekly intervals. The reverse transcriptase data is summarized below. The cultures treated with the 2-(2-thienyl)-imidazolo [4,5-b]pyridine showed no indication of resistance developing by day 186 at the 15 and 30 μg/ml level. CEMRF is a chronic HIV cell line.

| Day | 4 | 11 | 18 | 25 | 32 | 39 | 46 | 53 |
|---|---|---|---|---|---|---|---|---|
| No Drug | 12334 | 155438 | 18499 | 17679 | 10919 | 16969 | 12730 | 14630 |
| 7 μg/ml | 6521 | 9246 | 18882 | 12916 | 10484 | 8873 | 12096 | 15008 |
| 15 μg/ml | 6015 | 8997 | 17408 | 10044 | 6069 | 5047 | 4821 | 7961 |
| 30 μg/ml | 2727 | 5314 | 13701 | 4235 | 1442 | 3302 | 1156 | 2873 |
| Day | 60 | 67 | 74 | 71 | 88 | 95 | 102 | 109 |
| No Drug | 9966 | 8361 | 9402 | 9414 | 9442 | 8341 | 9542 | 6228 |
| 7 μg/ml | 9243 | 9241 | 8643 | 8422 | 8439 | 8435 | 8579 | 6440 |
| 15 μg/ml | 4323 | 3210 | 5620 | 4821 | 5124 | 2293 | 3205 | 2138 |
| 30 μg/ml | 1141 | 1281 | 1843 | 1209 | 1442 | 1687 | 1759 | 824 |

This test was run through 242 days and the data remained consistent.

EXAMPLE 4

CEMIIIB

A long term in vitro study of 2-(2-thienyl)-imidazolo [4,5-b]pyridine against an HIV-1 cell line, CEMIIIB was conducted at three different levels. The results with CEIIIB cells were reported at weekly intervals. The reverse transcriptase data is summarized below. The CEMIIIB is a viral strain of the CEMSS cell line and is a chronic HIV cell line.

| Day | 4 | 11 | 18 | 25 | 32 | 39 | 46 | 53 |
|---|---|---|---|---|---|---|---|---|
| No Drug | 4020 | 3447 | 1165 | 1060 | 1584 | 1332 | 1522 | 1402 |
| 7 μg/ml | 4631 | 4222 | 843 | 1052 | 1456 | 4298 | 1643 | 1458 |
| 15 μg/ml | 5622 | 1828 | 683 | 741 | 1005 | 948 | 1361 | 1281 |
| 30 μg/ml | 1968 | 2145 | 554 | 436 | 712 | 520 | 281 | 543 |
| Day | 60 | 67 | 74 | 71 | 88 | 95 | 102 | 109 |
| No Drug | 1382 | 1842 | 2161 | 2061 | 1611 | 1402 | 1560 | 1265 |
| 7 μg/ml | 1409 | 1903 | 1980 | 1832 | 1520 | 1367 | 1497 | 1165 |
| 15 μg/ml | 679 | 1251 | 1361 | 1241 | 1201 | 562 | 1043 | 1036 |
| 30 μg/ml | 406 | 391 | 651 | 281 | 241 | 102 | 256 | 376 |

This test was run through 242 days and the data remained consistent.

When the hydrochloride salt of 2-(2-thienyl)-imidazolo [4,5-b]pyridine was tested in the same manner, similar results were obtained through 60 days.

EXAMPLE 5

CEMROD

A long term in vitro study of 2-(2-thienyl)-imidazolo [4,5-b]pyridine against an HIV-2 cell line, CEMROD was conducted at three different levels. The results with CEMROD cells were reported at weekly intervals. The reverse transcriptase data is summarized below.

| Day      | 4    | 11    | 18   | 25   | 32   | 39   | 46   | 53    |
|----------|------|-------|------|------|------|------|------|-------|
| No Drug  | 8118 | 10003 | 7558 | 5099 | 6498 | 7860 | 6430 | 7630  |
| 7 µg/ml  | 8506 | 9471  | 6147 | 6302 | 5482 | 7253 | 4822 | 7257  |
| 15 µg/ml | 7447 | 8887  | 5399 | 5040 | 4695 | 6277 | 2165 | 6546  |
| 30 µg/ml | 4426 | 7092  | 3322 | 3212 | 3960 | 4543 | 1245 | 2402  |

| Day      | 60   | 67   | 74   | 71   | 88    | 95   | 102  | 109   |
|----------|------|------|------|------|-------|------|------|-------|
| No Drug  | 6714 | 6435 | 5161 | 8588 | 9596  | 6431 | 7632 | 12791 |
| 7 µg/ml  | 7019 | 7215 | 6240 | 9052 | 10053 | 7482 | 8023 | 13890 |
| 15 µg/ml | 5940 | 3215 | 4687 | 7256 | 8277  | 5116 | 6546 | 10349 |
| 30 µg/ml | 2410 | 1843 | 1285 | 2121 | 2543  | 2245 | 2402 | 1140  |

This test was run through 242 days and the data remained consistent.

EXAMPLE 6

U937IIIB

A long term in vitro study of 2-(2-thienyl)-imidazolo[4,5-b]pyridine against an HIV-1 cell line, U937IIIB was conducted at three different levels. The results with U937IIIB cells were reported at weekly intervals. The reverse transcriptase data is summarized below.

| Day      | 4    | 11   | 18   | 25   | 32   | 39   | 46   | 53   |
|----------|------|------|------|------|------|------|------|------|
| No Drug  | 2233 | 2245 | 2345 | 2358 | 2861 | 2498 | 1506 | 1325 |
| 7 µg/ml  | 2100 | 2205 | 2245 | 2212 | 2347 | 2516 | 1968 | 1695 |
| 15 µg/ml | 1188 | 713  | 993  | 1900 | 2003 | 1326 | 987  | 1221 |
| 30 µg/ml | 996  | 180  | 417  | 588  | 716  | 625  | 542  | 208  |

| Day      | 60   | 67   | 74   | 71   | 88   | 95   | 102  | 109  |
|----------|------|------|------|------|------|------|------|------|
| No Drug  | 2972 | 2169 | 6012 | 7798 | 7633 | 5813 | 5478 | 6425 |
| 7 µg/ml  | 2887 | 4170 | 6119 | 7786 | 6880 | 5041 | 5072 | 7437 |
| 15 µg/ml | 1205 | 2314 | 5689 | 4265 | 6832 | 4988 | 3912 | 4294 |
| 30 µg/ml | 504  | 782  | 1059 | 1414 | 1811 | 1988 | 1695 | 1542 |

This test was run through 242 days and the data remained consistent.

EXAMPLE 7

U937RF

A long term in vitro study of 2-(2-thienyl)-imidazolo[4,5-b]pyridine against U937RF, a protease resistant strain, was conducted at three different levels. The results with U937RF cells were reported at weekly intervals. The reverse transcriptase data is summarized below.

| Day      | 4    | 11   | 18   | 25   | 32   | 39    | 46   | 53   |
|----------|------|------|------|------|------|-------|------|------|
| No Drug  | 7189 | 9332 | 5299 | 6405 | 8233 | 12085 | 6810 | 7936 |
| 7 µg/ml  | 9711 | 9974 | 7462 | 6952 | 9161 | 11155 | 5178 | 5878 |
| 15 µg/ml | 6397 | 8051 | 7932 | 5229 | 7277 | 12487 | 4703 | 4960 |
| 30 µg/ml | 4841 | 5389 | 6988 | 6061 | 7572 | 8558  | 3065 | 3643 |

| Day      | 60   | 67   | 74   | 71   | 88   | 95   | 102  | 109   |
|----------|------|------|------|------|------|------|------|-------|
| No Drug  | 7933 | 7781 | 5082 | 7755 | 6939 | 5222 | 5682 | 4387  |
| 7 µg/ml  | 7586 | 6678 | 5927 | 7299 | 6996 | 5624 | 6002 | 13890 |
| 15 µg/ml | 7952 | 6417 | 5903 | 7016 | 5887 | 4602 | 5229 | 5718  |
| 30 µg/ml | 3445 | 4368 | 3639 | 1498 | 2697 | 2442 | 2815 | 2095  |

This test was run through 242 days and the data remained consistent.

When the hydrochloride salt of 2-(2-thienyl)-imidazolo[4,5-b]pyridine was tested in the same manner, similar results were obtained through 60 days.

Similar results are obtained with U937KN1272, a protease resistant strain, reported below.

| Day      | 4    | 11    | 18    | 25    | 32    | 39   | 46    | 53    |
|----------|------|-------|-------|-------|-------|------|-------|-------|
| No Drug  | 2803 | 8143  | 13911 | 14488 | 8058  | 9622 | 10781 | 13432 |
| 7 µg/ml  | 3503 | 10001 | 14176 | 14084 | 9919  | 8890 | 9238  | 9074  |
| 15 µg/ml | 2354 | 7962  | 11866 | 13386 | 10413 | 8675 | 8124  | 7645  |
| 30 µg/ml | 1209 | 4377  | 6376  | 9293  | 9903  | 6852 | 2502  | 2760  |

| Day      | 60   | 67   | 74   | 71   | 88   | 95   | 102  | 109  |
|----------|------|------|------|------|------|------|------|------|
| No Drug  | 7232 | 8421 | 9112 | 8221 | 9321 | 9248 | 9468 | 9899 |
| 7 µg/ml  | 7460 | 7863 | 8976 | 8402 | 8522 | 9358 | 9221 | 8245 |
| 15 µg/ml | 5534 | 4321 | 6974 | 5364 | 4297 | 5224 | 5361 | 7833 |
| 30 µg/ml | 2478 | 1643 | 3270 | 4820 | 3184 | 2031 | 3427 | 1356 |

This test was continued through 242 days and similar results were obtained.

When the hydrochloride salt of 2-(2-thienyl)-imidazolo [4,5-b]pyridine was tested in the same manner, similar results were obtained through 60 days.

EXAMPLE 8

Hepatitis

In an in vitro virus production test of hepatitis B, HEPG2 2.2.15 the following results were obtained with 2-(2-thienyl)-imidazolo [4,5-b]pyridine.

| Conc. µg/ml | 200 | 64 | 20 | 6.4 | 2 | 0.64 | 0 |
|---|---|---|---|---|---|---|---|
| DNA Copy Number (per 3 µl) | | | | | | | |
| sample 1 | 0.3 | 1.2 | 8.2 | 44.3 | 134.5 | 249.2 | 361.3 |
| sample 2 | 0.0 | 0.0 | 0.0 | 13.3 | 124.2 | 255.9 | 357.0 |
| sample 3 | 0.1 | 0.0 | 0.0 | 26.1 | 145.8 | 261.6 | 299.3 |
| mean | 0.1 | 0.4 | 2.7 | 27.9 | 134.8 | 255.6 | 339.2 |
| % virus control | 0 | 0.1 | 0.8 | 8.2 | 39.8 | 75.3 | 100 |
| Toxicity Values | | | | | | | |
| sample 1 | 0.018 | 0.017 | 0.404 | 1.249 | 1.121 | 1.389 | 1.146 |
| sample 2 | 0.017 | 0.018 | 0.389 | 1.157 | 1.246 | 1.334 | 1.249 |
| sample 3 | 0.017 | 0.017 | 0.361 | 1.407 | 1.432 | 1.355 | 1.363 |
| mean | 0.017 | 0.017 | 0.385 | 1.271 | 1.266 | 1.359 | 1.253 |
| % cell control | 1.4 | 1.4 | 30.7 | 101.5 | 101.1 | 108.5 | 100 |

The $IC_{50}$ is 1.6 µg/ml; the $TC_{50}$ is 16.3 µg/ml and the therapeutic index or TI is 10.1.

In a replicate experiment, the $IC_{50}$ is 10.71 µg/ml; the $TC_{50}$ is 16.8 µg/ml, and the TI is 23.4.

For comparison 3TC was tested and the following data were obtained:

| Conc. µg/ml | 1 | 0.32 | 0.1 | 0.032 | 0.01 | 0.0032 | 0 |
|---|---|---|---|---|---|---|---|
| DNA Copy Number (per 3 µl) | | | | | | | |
| sample 1 | 6.0 | 36.7 | 73.0 | 192.6 | 286.1 | 265.4 | 308.6 |
| sample 2 | 3.9 | 45.1 | 74.8 | 243.2 | 192.3 | 328.0 | 304.5 |
| sample 3 | 2.1 | 56.5 | 60.5 | 255.3 | 276.7 | 247.9 | 246.8 |
| mean | 4.0 | 46.1 | 69.4 | 230.4 | 251.7 | 280.4 | 286.7 |
| % virus control | 1.4 | 13.1 | 24.2 | 80.4 | 87.8 | 97.8 | 100.0 |
| Toxicity Values | | | | | | | |
| sample 1 | 1.423 | 1.082 | 1.151 | 1.074 | 1.001 | 1.009 | 1.146 |
| sample 2 | 1.256 | 1.207 | 1.220 | 1.153 | 1.081 | 1.173 | 1.249 |
| sample 3 | 1.322 | 1.227 | 1.200 | 1.316 | 1.099 | 1.230 | 1.363 |
| mean | 1.334 | 1.172 | 1.190 | 1.181 | 1.060 | 1.137 | 1.253 |
| % cell control | 106.5 | 93.6 | 95.0 | 94.3 | 84.6 | 90.8 | 100.0 |

The $IC_{50}$ is 0.089 µg/ml; the $TC_{50}$ is >1 µg/ml and the TI is 14.6.

In a replicate experiment, the $IC_{50}$ is 0.021 µg/ml; the $TC_{50}$ is >1 µg/ml and the TI is >47.6.

2-(2-thienyl)-imidazolo [4,5-b]pyridine can be used to treat hepatitis B.

EXAMPLE 9

Herpes Simplex Testing 2-(2-thienyl)-imidazolo [4,5-b]pyridine was tested against HSV-2MS, a herpes simplex virus-2 in vero cells and compared with Acyclovir. The $IC_{50}$ for Acyclovir is 0.81 and 0.85 in a replicate study. The $TC_{50}$ is >1 and the TI or therapeutic index is >1.2. For 2-(2-thienyl)-imidazolo [4,5-b]pyridine the $IC_{50}$ is 62.1 the $TC_{50}$ is 82.8 and the TI or therapeutic index is 1.3.

EXAMPLE 10

Kaposi's Sarcoma 2-(2-thienyl)-imidazolo [4,5-b]pyridine was tested against Kaposi's Sarcoma, a herpes virus, in vitro using the Humam Herpes Virus 8 (HHV8) cell line, TPA-induced BCBL-1 cells. The DNA copy number and the toxicity value were measured and compared with Cidofovir. Kaposi's sarcoma (KS) is a cancer that is often found in people with weak immune systems, such as those taking immunosuppressants or those with AIDS. The exact nature of the disease is uncertain, but it is almost always found in association with HHVS8. Recent studies suggest that KS is caused by the herpes virus; that is, that KS is a herpes virus that manifests itself as a cancer.

| Conc. µM | 25 | 8 | 2.5 | 0.8 | 0.25 | 0.08 | 0 |
|---|---|---|---|---|---|---|---|
| DNA Copy Number (per 3 µl) | | | | | | | |
| sample 1 | 0 | 8.9 | 1329.8 | 7521 | 6668.9 | 8485.1 | 8855.9 |
| sample 2 | 0.0 | 0.0 | 1198.3 | 5985.4 | 6336.3 | 7948.1 | 9744.2 |
| sample 3 | 0.0 | 0.0 | 1275.7 | 1819.5 | 6995.5 | 9000.8 | 8075.7 |
| average | 0.0 | 3.0 | 1276.9 | 5108.6 | 6666.9 | 8478.0 | 8891.9 |
| % virus control | 0.0 | 0.0 | 14.3 | 57.5 | 75.0 | 95.3 | 100.0 |
| Toxicity Values | | | | | | | |
| sample 1 | 0.443 | 0.639 | 0.794 | 0.824 | 0.867 | 0.864 | 0.954 |
| sample 2 | 0.398 | 0.700 | 0.684 | 0.770 | 0.819 | 0.797 | 0.924 |
| sample 3 | 0.447 | 0.677 | 0.704 | 0.814 | 0.934 | 0.780 | 1.030 |
| average | 0.430 | 0.672 | 0.728 | 0.803 | 0.874 | 0.814 | 0.970 |
| % cell control | 4403 | 69.3 | 75.0 | 82.8 | 90.1 | 83.9 | 100.0 |

$IC_{50}$ µM=1.1
$TC_{50}$ µM=21.1
TI=19.2

Data for 2-(2-thienyl)-imidazolo [4,5-b]pyridine

| Conc. µM | 200 | 64 | 20 | 6.4 | 2 | 0.64 | 0 |
|---|---|---|---|---|---|---|---|
| DNA Copy Number (per 3 µl) | | | | | | | |
| sample 1 | 1680.4 | 615.0 | 11619.4 | 11795.6 | 13427.5 | 16524.7 | 14173.6 |
| sample 2 | 2041.2 | 510.3 | 15173.8 | 15297.5 | 11819.4 | 16524.9 | 13576.8 |
| sample 3 | 2340.8 | 156.6 | 7172.3 | 14536.1 | 15714.5 | 12316.8 | 15824.5 |
| average | 2020.8 | 427.3 | 11321.8 | 13876.4 | 13653.8 | 14122.1 | 14525.0 |
| % virus control | 13.9 | 2.9 | 77.9 | 95.5 | 94.0 | 97.2 | 100.0 |
| Toxicity Values | | | | | | | |
| sample 1 | 0.068 | 0.020 | 0.701 | 1.198 | 1.155 | 1.034 | 1.059 |
| sample 2 | 0.067 | 0.016 | 0.706 | 1.119 | 1.182 | 1.201 | 1.056 |

-continued

| Conc. µM | 200 | 64 | 20 | 6.4 | 2 | 0.64 | 0 |
|---|---|---|---|---|---|---|---|
| sample 3 | 0.067 | 0.013 | 0.782 | 1.193 | 1.179 | 1.245 | 1.034 |
| average | 0.067 | 0.016 | 0.729 | 1.170 | 1.172 | 1.160 | 1.049 |
| % cell control | 6.4 | 1.5 | 69.5 | 111.5 | 111.7 | 110.5 | 100.0 |

$IC_{50}$ µM=36.4
$TC_{50}$ µM=32.6

EXAMPLE 11

Anti-fungal Activity 2-(2-thienyl)-imidazolo [4,5-b]pyridine was tested against a number of fungi in vitro. It was active against *Cryptococcus neoformans* and *Curvularia lunata*. The cidal activity for the *C. neoformans* is high enough that it is clear static against this yeast. This test was conducted using a method based upon NCCLS reference method M-27A published in 1997. Solvent, medium and growth controls were set-up with the tests. Once these were read to validate the test performance, the QC fungi were read to insure they had expected results. These steps validated the test system. DMSO was used as a drug-chemical solvent. These test were read following incubation at 35° C. when the QC organisms (Candida spp.) showed good growth. MIC values were concentrations in which growth was inhibited or reduced at least 90% in comparison to the control growth. The 90% cut-off is necessary for azoles, which are static and not cidal. The FMC or cidal level was determined by sub-culturing a sample from each tube showing no growth.

*Curvularia lunata* causes mycotic keratitis, sinus and deep organ infections. It is opportunistic in immunocompromised patients.

*Cryptococcus neoformans* is an opportunistic pathogen involving the central nervous system in AIDS patients and is a yeast having protective polysaccharide capsule that is a basidiomycete.

The abbreviations used for the compounds tested are:

AmB is amphotericin B
Thia is thiabendazole
Methyl is methyl 1,2-benzimidazole carbamate or benomyl
Itra is Itraconazole
THP is 2-(2-thienyl)-imidazolo [4,5-b]pyridine

TABLE 6

| THP | AmB | Thia | Methyl | Itra |
|---|---|---|---|---|
| MIC data (µg/ml) *Curvularia lunata* | | | | |
| 0.03 | 0.03 | ≧32 | 0.06 | 0.03 |
| MIC data (µg/ml) | | | | |

TABLE 6-continued

| THP | AmB | Thia | Methyl | Itra |
|---|---|---|---|---|
| *Cryptococcus neoformans* | | | | |
| 0.03 | 0.25 | 16 | 8 | 0.03 |
| MFC data (µg/ml) *Cryptococcus neoformans* | | | | |
| >32 | 1 | >32 | >32 | >32 |

What is claimed is:

1. A method of treating a viral infection comprising administering to a patient in need thereof a therapeutically effective amount of a 2-thienyl imidazolo[4,5]pyridine having the formula:

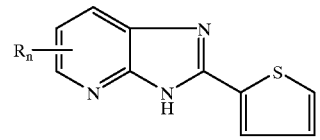

wherein, n is from 1 to 3; and

R is selected from the group consisting of hydrogen, alkyl having from 1 to 7 carbon atoms, chloro, bromo, fluoro, oxychloro, hydroxy, sulfhydryl, and alkoxy having the formula —O(CH$_2$)$_y$CH$_3$ wherein y is from 0 to 6.

2. A method according to claim 1 wherein said viral infection is selected from the group consisting of HIV, herpes simplex, hepatitis, and HHV8.

3. A method according to claim 2 wherein said viral infection is hepatitis B or hepatitis C.

4. A method according to claim 2 wherein said viral infection is HIV.

5. A method according to claim 2 comprising administering a therapeutically effective amount of a pharmaceutical composition comprising said 2-thienyl-imidazolo[4,5] pyridine.

6. A method according to claim 5 which comprises administering to a patient in need thereof from about 1 mg/kg to about 10,000 mg/kg of said 2-thienyl imidazolo [4,5]pyridine.

7. A method according to claim 5 wherein said 2-thienyl imidazolo[4,5]pyridine is in the form of a pharmaceutical addition salt thereof.

8. A method according to claim 7 wherein said pharmaceutical addition salt is a hydrochloride salt.

9. A method according to claim 5 wherein said 2-thienyl imidazolo[4,5]pyridine derivative is in the form of a prodrug thereof.

10. A method according to claim 1 wherein said method comprises administering a therapeutic agent in a combination therapy with said 2-thienyl imidazolo[4,5]pyridine.

11. A method according to claim 10 wherein said viral infection is HIV and wherein said therapeutic agent is selected from the group consisting of AZT, TC-3, and protease inhibitors.

12. A method according to claim 1 wherein said 2-thienyl imidazolo [4,5]pyridine is administered in a solid form and wherein said solid form includes a carrier selected from the group consisting of lactose, sucrose, gelatin, cyclodextrin, cyclodextrin derivatives and agar.

13. A method according to claim 12 wherein from about 10 mg/kg body weight to about 6000 mg/kg body weight of said 2-thienyl imidazolo [4,5]pyridine is administered.

14. A method according to claim 1 wherein said 2-thienyl imidazolo[4,5]pyridine is administered in a liquid form and wherein said liquid form is selected from the group consisting of an aqueous solution, an alcohol solution, an emulsion, a suspension, a suspension reconstituted from non-effervescent or effervescent preparations, and a suspension in pharmaceutically acceptable fats or oils.

15. A method according to claim 1 wherein said 2-thienyl imidazolo[4,5]pyridine is in the form of a pharmaceutical addition salt thereof.

16. A method according to claim 5 wherein said pharmaceutical addition salt is a chloride.

17. A method according to claim 1 wherein said 2-thienyl imidazolo[4,5]pyridine is in the form of a prodrug thereof.

18. A method according to claim 1 wherein said 2-thienyl imidazolo[4,5]pyridine is in the form of a liposome delivery system.

19. A method according to claim 1 wherein said method comprises administering a therapeutic agent in a combination therapy with said 2-(2-thienyl)imidazolo[4,5-b]pyridine wherein said therapeutic agent is selected from the group consisting of AZT, TC-3, protease inhibitors, acyclovir, famiciclovir, valacyclovir, Ribavirin, interferon, a combination of Ribavirin and interferon, a combination of Ribavirin and beta globulin, a recombinant alpha interferon, and mixtures thereof.

20. A method of treating a viral infection comprising administering to a patient in need thereof a therapeutically effective amount of 2-(2-thienyl)imidazolo[4,5-b]pyridine, having the formula:

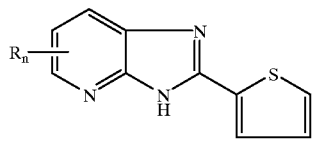

wherein n is 3, and R is hydrogen.

21. A method according to claim 20 wherein said viral infection is selected from the group consisting of HIV, herpes simplex, hepatitis, and HHV8.

22. A method according to claim 20 wherein said viral infection is hepatitis B or hepatitis C.

23. A method according to claim 20 wherein said 2-(2-thienyl)imidazolo[4,5-b]pyridine is administered in an amount of from about 1 mg/kg to about 6000 mg/kg.

24. A method according to claim 23 wherein said method comprises administering a therapeutic agent in a combination therapy with said 2-(2-thienyl)imidazolo[4,5-b]pyridine wherein said therapeutic agent is selected from the group consisting of AZT, TC-3, protease inhibitors, acyclovir, famiciclovir, valacyclovir, Ribavirin, interferon, a combination of Ribavirin and interferon, a combination of Ribavirin and beta globulin, a recombinant alpha interferon, and mixtures thereof.

25. A method according to claim 20 wherein said 2-(2-thienyl)imidazolo[4,5-b]pyridine is in the form of a pharmaceutical addition salt thereof.

26. A method according to claim 25 wherein said pharmaceutical addition salt is a hydrochloride salt.

27. A method according to claim 20 wherein said 2-(2-thienyl)imidazolo[4,5-b]pyridine is in the form of a prodrug thereof.

28. A method according to claim 20 wherein said 2-(2-thienyl)imidazolo[4,5-b]pyridine is in the form of a liposome delivery system.

29. A method according to claim 20 wherein said viral infection is herpes simplex.

30. A method according to claim 20 wherein said viral infection is HIV.

31. A method of treating a fungal infection comprising administering to a patient in need thereof a therapeutically effective amount of a 2-thienyl imidazolo[4,5]pyridine having the formula:

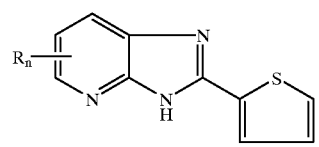

wherein, n is from 1 to 3; and

R is selected from the group consisting of hydrogen, alkyl having from 1 to 7 carbon atoms, chloro, bromo, fluoro, oxychloro, hydroxy, sulfhydryl, and alkoxy having the formula —O(CH$_2$)$_y$CH$_3$ wherein y is from 0 to 6.

32. A method according to claim 31 wherein said 2-thienyl imidazolo[4,5]pyridine has the formula:

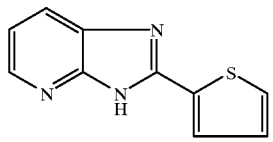

or a pharmaceutically acceptable salt thereof.

33. A method according to claim 32 wherein said 2-thienyl imidazolo[4,5]pyridine is administered in an amount of from about 1 mg/kg to about 6000 mg/kg.

34. A method according to claim 31 wherein said 2-thienyl imidazolo[4,5]pyridine derivative is in the form of a pharmaceutical addition salt thereof.

35. A method according to claim 34 wherein said pharmaceutical addition salt is a hydrochloride salt.

36. A method according to claim 31 wherein said 2-thienyl imidazolo[4,5]pyridine derivative is in the form of a prodrug thereof.

37. A method according to claim 31 wherein said 2-thienyl imidazolo[4,5]pyridine is administered in an amount of from about 1 mg/kg to about 10,000 mg/kg.

38. A method of treating Kaposi's sarcoma comprising administering to a patient in need thereof a therapeutically effective amount of a 2-thienyl imidazolo[4,5]pyridine having the formula:

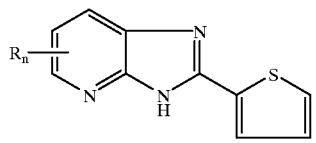

wherein,
  n is from 1 to 3; and
  R is selected from the group consisting of hydrogen, alkyl having from 1 to 7 carbon atoms, chloro, bromo, fluoro, oxychloro, hydroxy, sulfhydryl, and alkoxy having the formula $-O(CH_2)_y CH_3$ wherein y is from 0 to 6.

39. A method according to claim 38 wherein said 2-thienyl imidazolo[4,5]pyridine derivative is in the form of a pharmaceutical addition salt thereof.

40. A method according to claim 39 wherein said pharmaceutical addition salt is a hydrochloride salt.

41. A method according to claim 38 wherein said 2-thienyl imidazolo[4,5]pyridine derivative is in the form of a prodrug thereof.

42. A method according to claim 38 wherein said 2-thienyl imidazolo[4,5]pyridine is administered in an amount of from about 1 mg/kg to about 10,000 mg/kg.

43. A method according to claim 38 wherein said 2-thienyl imidazolo[4,5]pyridine has the formula:

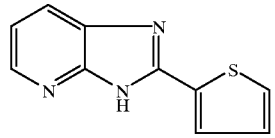

or a pharmaceutically acceptable salt thereof.

* * * * *